United States Patent
Bowman et al.

(10) Patent No.: US 8,454,525 B2
(45) Date of Patent: Jun. 4, 2013

(54) SYSTEM FOR QUANTIFYING BLOOD FLOW IN TISSUE AND UPDATING TISSUE BASELINE CONDITIONS

(75) Inventors: H. Frederick Bowman, Needham, MA (US); Gregory T. Martin, Cambridge, MA (US)

(73) Assignee: Thermal Technologies, Inc., Cambridge, MA (US)

( * ) Notice: Subject to any disclaimer, the term of this patent is extended or adjusted under 35 U.S.C. 154(b) by 389 days.

(21) Appl. No.: 12/800,880

(22) Filed: May 25, 2010

(65) Prior Publication Data

US 2010/0241016 A1 Sep. 23, 2010

Related U.S. Application Data

(62) Division of application No. 10/406,829, filed on Apr. 4, 2003, now Pat. No. 7,758,511.

(60) Provisional application No. 60/403,496, filed on Aug. 14, 2002, provisional application No. 60/370,483, filed on Apr. 5, 2002.

(51) Int. Cl.
*A61B 5/02* (2006.01)
*A61B 18/04* (2006.01)

(52) U.S. Cl.
USPC .............................. 600/504; 600/481; 606/27

(58) Field of Classification Search
USPC ........................ 600/481, 483, 484, 500–507
See application file for complete search history.

(56) References Cited

U.S. PATENT DOCUMENTS

| | | | |
|---|---|---|---|
| 3,789,831 A | 2/1974 | Kopaniky |
| 3,918,434 A | 11/1975 | Lubbers |
| 4,059,982 A | 11/1977 | Bowman |
| RE30,317 E | 7/1980 | Lubbers |
| 4,228,805 A | 10/1980 | Rosen |
| 4,230,122 A | 10/1980 | Lubbers |
| 4,403,615 A | 9/1983 | Hoehner |
| 4,739,771 A | 4/1988 | Manwaring |
| 4,852,027 A | 7/1989 | Bowman |
| 4,859,078 A | 8/1989 | Bowman |
| 5,035,514 A | 7/1991 | Newman |
| 5,038,304 A | 8/1991 | Bonne |
| 5,078,137 A | 1/1992 | Edell |
| 5,146,414 A | 9/1992 | McKowan |
| 5,261,411 A | 11/1993 | Hughes |
| 5,277,191 A | 1/1994 | Hughes |
| 5,425,868 A | 6/1995 | Pedersen |
| 5,474,080 A | 12/1995 | Hughes |
| 5,682,899 A | 11/1997 | Nashef |
| 5,860,922 A | 1/1999 | Gordon |
| 5,988,875 A | 11/1999 | Gershfeld |
| 6,190,378 B1 | 2/2001 | Jarvinen |
| 6,203,501 B1 | 3/2001 | Bowman |
| 6,221,025 B1 | 4/2001 | Skoletsky |
| 6,488,677 B1 | 12/2002 | Bowman |
| 6,805,672 B2 | 10/2004 | Martin |
| 7,267,651 B2 | 9/2007 | Nelson |
| 2001/0000792 A1 | 5/2001 | Bowman |
| 2002/0169388 A1 | 11/2002 | Bowman |
| 2002/0173731 A1 | 11/2002 | Martin |
| 2003/0120162 A1 | 6/2003 | Bowman |

*Primary Examiner* — Navin Natnithithadha
(74) *Attorney, Agent, or Firm* — James L. Neal

(57) ABSTRACT

Methods and apparatus for determining blood flow in tissue are disclosed. The methods and apparatus are used to establish a baseline for both thermal properties of the tissue and non-physiologic conditions. Periodic changes in either or both constituents of the baseline are determined and, when the changes correspond to a need for a new baseline, a new baseline is established.

19 Claims, 9 Drawing Sheets

SYSTEM FOR QUANTIFYING BLOOD FLOW IN TISSUE AND UPDATING TISSUE BASELINE CONDITIONS

SUMMARY OF THE INVENTION

The present invention covers technology developed to provide clinicians with a powerful prognostic tool for quantifying tissue blood flow (i.e., "perfusion") in continuous, real-time. The measurements made by the apparatus of the present invention have long been sought after and represent important parameters in the understanding and management of many critical medical situations, and prior to the development of this technology, the practical capability to get continuous, real-time, soft tissue perfusion measurements in absolute units, did not exist. The high clinical value of the technology behind this invention has been documented in life-saving neurosurgical and organ transplantation surgery cases, among others.

In the monitoring of perfusion in the tissue of a subject (i.e.: the flow of blood in a capillary bed) it is useful to have a continuous or nearly continuous stream of data over time. The accuracy of measurements is affected by various physiologic and instrument baseline changes. Thus, it is also useful to monitor baseline conditions and adjust for baseline shifts over time. The monitoring system surveys selected baseline factors that may adversely affect the integrity of the monitored data and uses the results to make corrections.

The continuous measurement of perfusion over time is valuable in many clinical settings. Among them are the measurement of perfusion in the brain of patients with traumatic brain injury to anticipate adverse conditions such as cerebral ischemia, the monitoring of perfusion in organ transplantation to assess ischemia caused by thrombotic and reperfusion injury and the monitoring of perfusion in flaps in reconstructive plastic surgery to assess tissue viability. The perfusion value is also an indicator of the presence or absence of shock and monitoring perfusion over time may permit the clinician to anticipate and treat shock.

Approximately 370,000 Americans suffer traumatic head injury annually. By using the apparatus of the present invention to measure continuous, real-time cerebral tissue blood flow, clinicians can identify patients at risk for ischemia due to vasospasm or cerebral edema (brain swelling), and measure the patient's tissue blood flow response to therapies implemented to correct the pathology. In addition, other critical neurosurgical interventions, such as aneurysm repair, tumor and arterial-veinous malfunction removal and procedures to relieve patients suffering from subarachnoid hemorrhage are among those that will also benefit from the valuable prognostic data provided by the apparatus of the present invention.

One embodiment, the Bowman Perfusion Monitor, Model 500, is a device that monitors tissue blood flow continuously at the capillary level in real-time and in absolute units of ml/100 g-min. The Model 500 perfusion-monitoring device utilizes thermal diffusion technology described here through its minimally invasive, QFlow 500 Probe, which physicians can implant in cerebral or any other soft tissue.

The present invention may be used over extended periods of time in living subjects and provide thermal property and perfusion data with a high degree of accuracy. This obtains even when tissue physiology is changing and the physiological changes are accompanied by changing thermal properties in the tissue. Thermal properties of particular interest are the properties of diffusivity and conductivity which are useful in the determination of tissue perfusion.

To accommodate physiological or non-physiological changes over time, the present invention provides methods and apparatus for determining baseline thermal conditions of the tissue at a selected location or site and for establishing baseline criteria to be used for the periodic updating of baseline tissue conditions (in situ calibration). The baseline tissue conditions or thermal properties may change with time. Thus, one or more steps are provided for periodically determining the need for updating to new baseline tissue conditions (in situ recalibration) as tissue conditions change.

Calibration or the establishing of a baseline may also take into account internal monitoring system parameters (artifacts). Recalibration or the establishing of a new baseline may include one or more steps for periodically determining parameter changes and, when changes are outside of an acceptable range, recognizing the need for new or updated baseline criteria. Accordingly baseline criteria are updated as the parameters and conditions unintentionally change.

The process of establishing a new or updated baseline may be manually initiated or the system may automatically self-adjust (i.e.: self-recalibrate). The instrument may self-adjust automatically and periodically when physiology changes by some predetermined amount or when a combination of physiologic conditions and system parameters change by a predetermined amount. The system monitors the parameters and conditions to determine when values have changed to be outside predetermined limits and recalculates baseline when limits are exceeded.

One embodiment of the present invention is directed to a method for the periodic updating of tissue baseline conditions in order to make perfusion measurements over extended periods during which tissue baseline conditions change as a consequence of multiple physiologic and non-physiologic factors. The method may comprise the following steps: (a) perform in situ calibration of a perfusion sensor in the tissue, that is, establish baseline tissue conditions; (b) make perfusion measurement in tissue and (c) automatically recognize conditions under which the in situ calibration is no longer valid. Examples of such conditions include physiologic conditions such as tissue and vascular damage, tissue edema, tissue scar formation, influence of a large vessel, change in vascular status, such as blood volume, vasodilation, and vasoconstriction; changes in perfusion; changes in blood pressure; changes in tissue pressure; changes in tissue temperature; changes in blood temperature; changes in tissue metabolism; and/or measurement of artifact conditions, such as sensor motion relative to the tissue, excessive sensor-tissue contact force inducing capillary collapse, insufficient sensor-tissue contact force resulting in artifactual transduction of perfusion, sensor cross-talk, ambient temperature changes, electrical interference, instrumentation drift. Following step (c), (d) automatically perform a recalibration, selected from one or more of the following to reestablish baseline conditions; probe recalibration and instrumentation recalibration; and (e) repeat the steps as necessary to maintain optimum operation.

BRIEF DESCRIPTION OF THE DRAWINGS

Certain preferred embodiments are described below with reference to the accompanying figures in which.

DETAILED DESCRIPTION OF THE PREFERRED EMBODIMENTS

Figure 1:
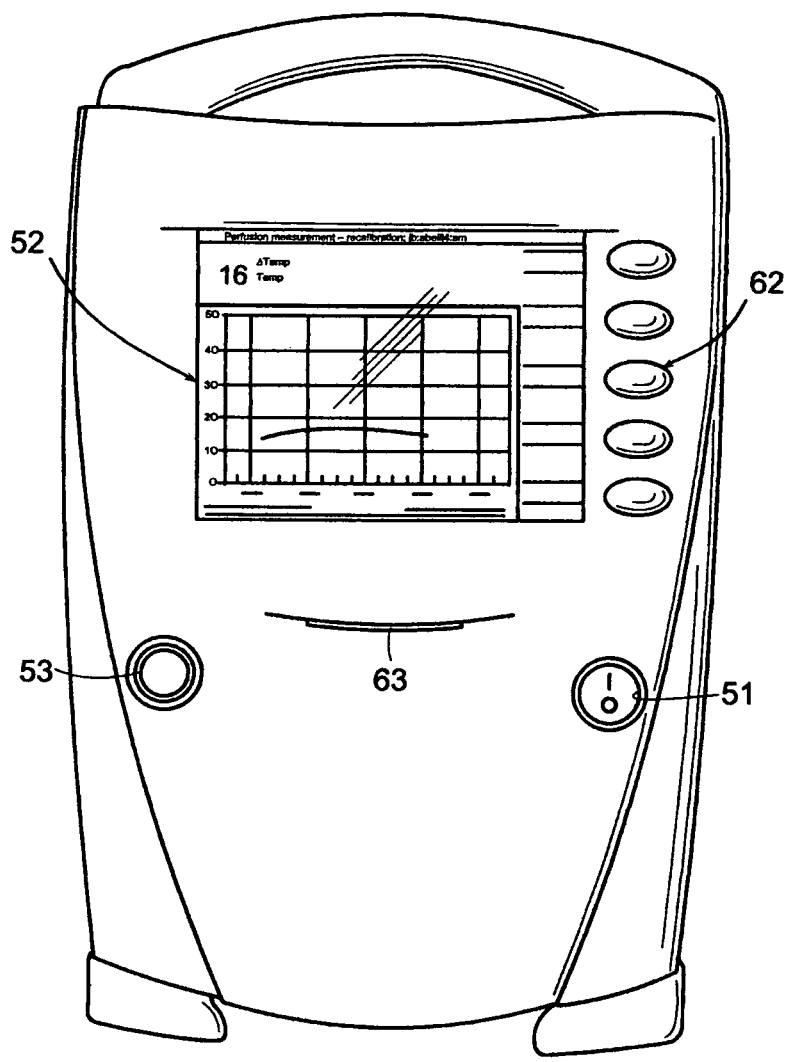
FIG. 1 is a front view depiction of an embodiment of the invention.
Figure 2:
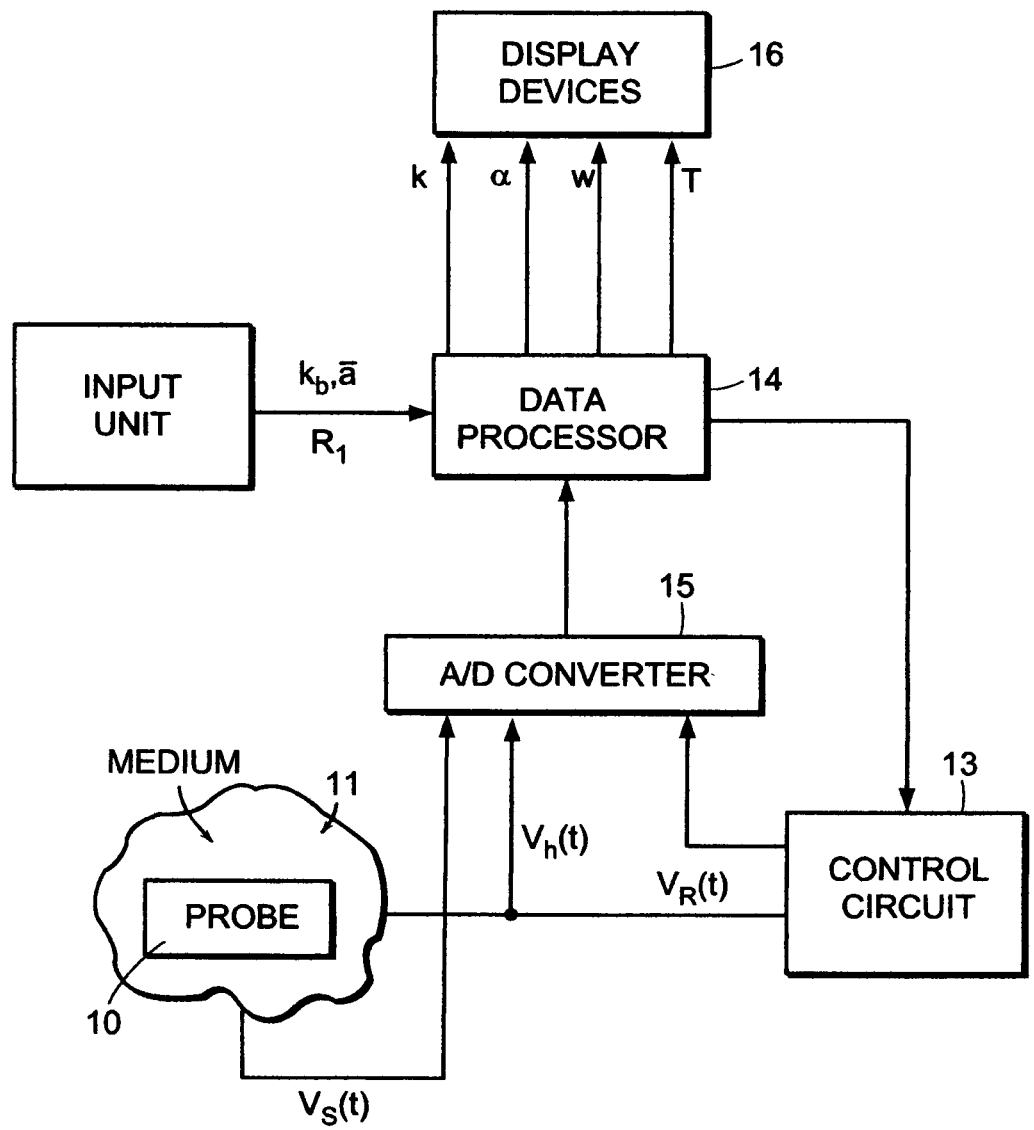
FIG. 2 is a block diagram of an embodiment of a system in which the disclosed techniques can be used.

This invention can be implemented by use of a system such as shown in FIG. 1 and illustrated schematically in FIG. 2. FIG. 1 shows the Bowman Perfusion Monitor with a display screen 52, a keyboard 62, connector 53 for a perfusion probe, a slot 63 to permit passage of a printed tape and an on/off switch 51. As explained in the Bowman patents referenced below and illustrated by FIG. 2, a probe 10 is immersed in a medium (e.g.: tissue) 11 and can be heated by a heater voltage $V_h(t)$ supplied via control circuit 13. The sensed voltage $V_s(t)$ from probe 10 is supplied to A/D converter 15 for supplying to a data processor 14 in digital form for suitable processing thereof in order to determine k (intrinsic thermal conductivity), $\alpha$ (diffusivity), and $\omega$ (flow rate or perfusion), the values of which can be displayed in a display device 16. The values of probe calibration constants $k_b$, a, and $R_i$ can be supplied via a suitable input unit that may be in the form of a memory chip. Such operation is essentially described in the aforesaid patents for a particular mathematical model described therein and the same system as generally depicted therein can also be used for a different mathematical model, the processing equations required to be implemented in data processor 14 being different depending on the mathematical model selected.

The method of determining properties of a medium by causing a thermal change in the medium and then calculating it's properties based on the medium's response to the thermal change is described in detail in U.S. Pat. No. 4,059,982 to H. F. Bowman issued on Nov. 29, 1977; U.S. Pat. No. 4,852,027 to H. F. Bowman and W. H. Newman issued on Jul. 25, 1989 and U.S. Pat. No. 5,035,514 to William H. Newman issued on Jul. 30, 1991.

Figure 3:
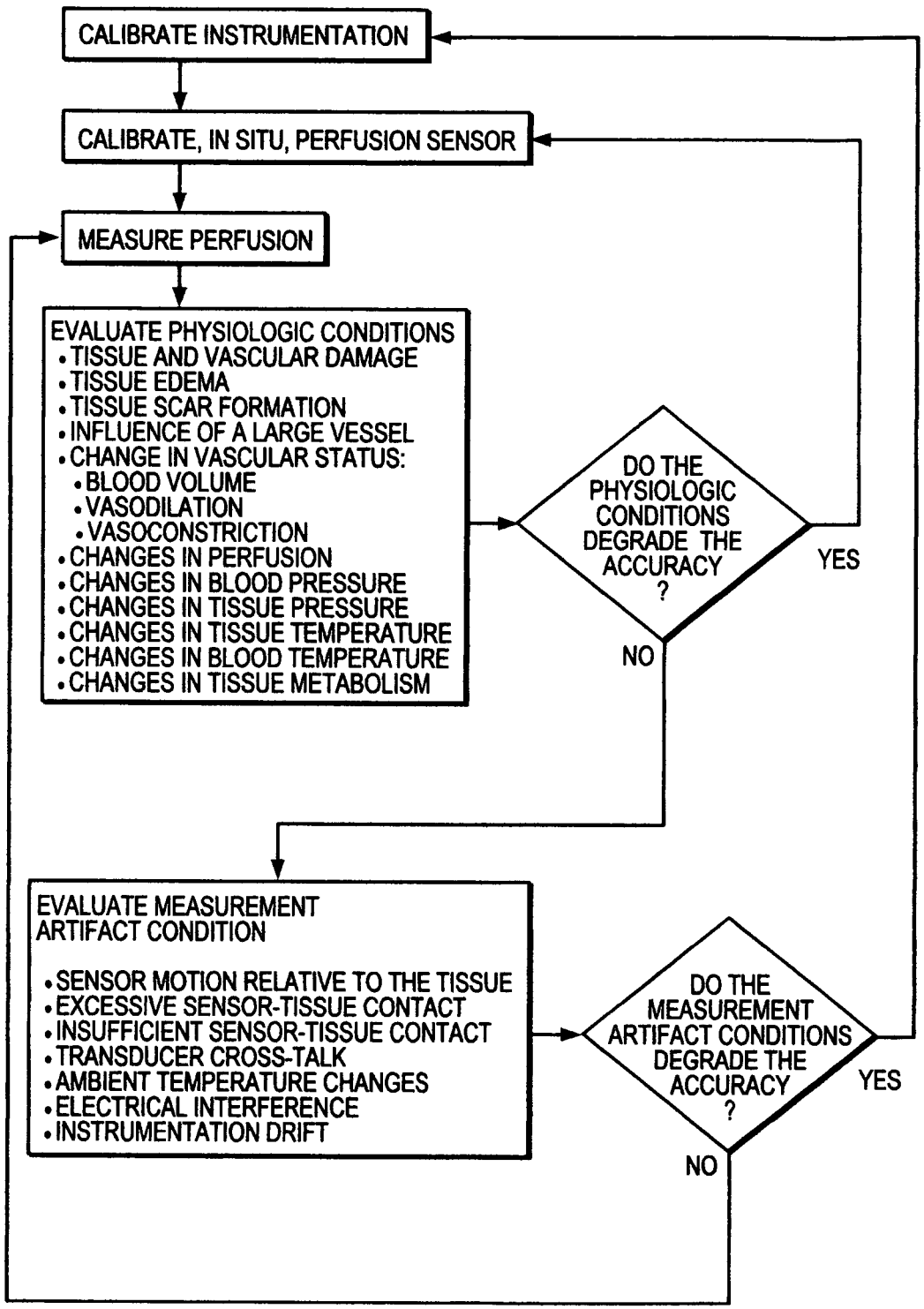
FIG. 3 is a flow chart of one embodiment of the present invention.
Figure 4:
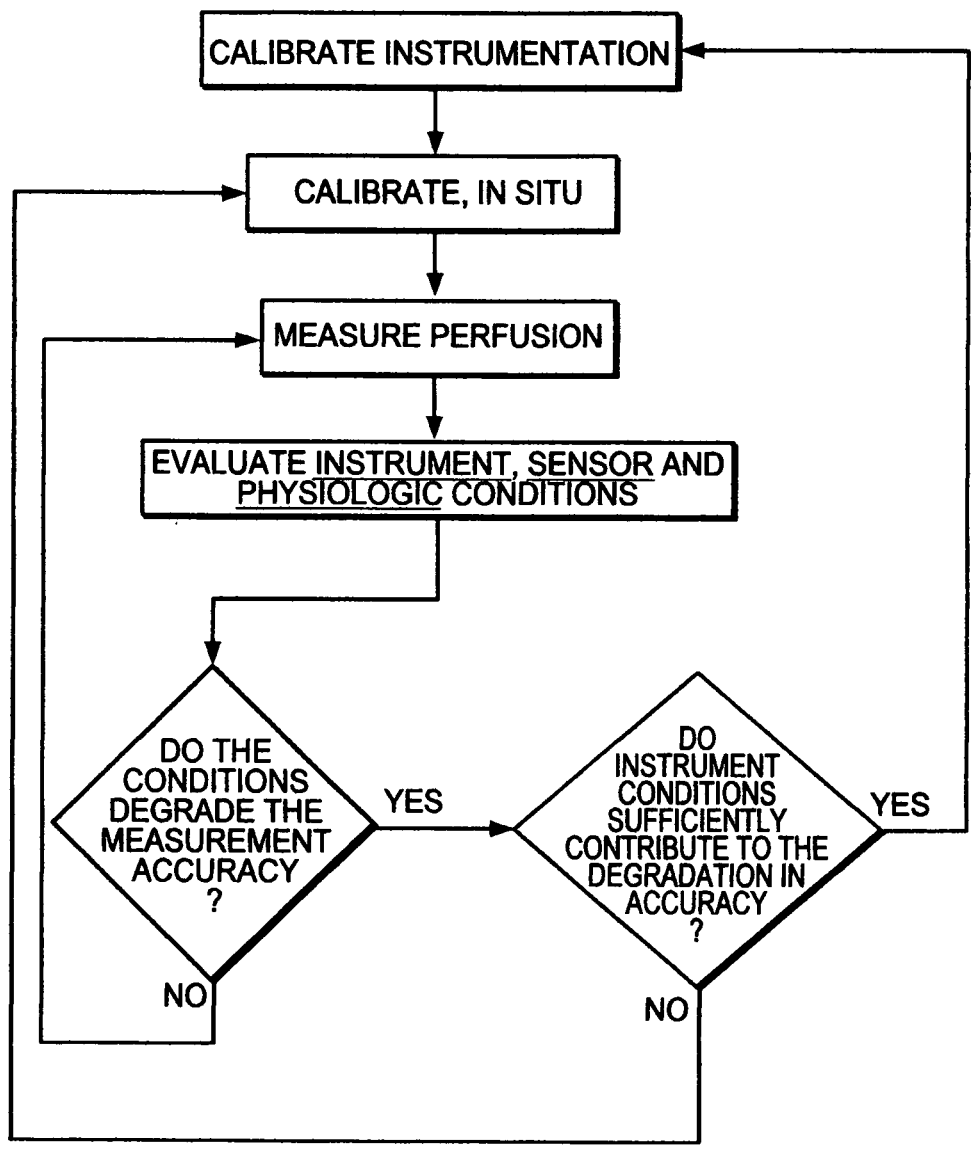
FIG. 4 is a flow chart of a system to repeatedly recalibrate thermal-based perfusion sensors.

As illustrated in FIGS. 3 and 4, methods and software apparatus are provided to repeatedly recalibrate thermal-based perfusion sensors and related instrumentation. The system monitors the conditions of the electronic instrument and conditions affecting the sensor and, via the sensor, also monitors the conditions of tissue, organ and the overall physiology of the subject to establish a baseline. When the weighted combination of conditions in the instrument and sensor and in the physiology of the subject fall outside a preset threshold, a perfusion measurement less accurate than desired is indicated and the system determines that a new baseline (recalibration) is needed. The system may monitor these conditions or use inputs from other devices that monitor physiologic or instrument conditions. The establishment of a new baseline (recalibration) may be initiated manually after the system prompts the operator or it may be automatically initiated by the system. Similarly, the system may also be prompted by an external apparatus to automatically perform part or all of the recalibration process.

The instrument conditions that are monitored include, but are not limited to; ambient temperature changes, electrical interference, and instrumentation drift. The thermal-based perfusion sensor conditions that are monitored include, but are not limited to; excessive sensor-tissue contact force that can result in capillary collapse, insufficient sensor-tissue contact force that can result in artifactual thermal transduction, sensor cross-talk, and movement of the sensor relative to the tissue. The physiologic conditions of the subject that are monitored include, but are not limited to; tissue and vascular damage, tissue edema, tissue scar formation, influence of a large vessel, change in vascular status (i.e.: blood volume, vasodilation, and vasoconstriction), changes in perfusion, changes in blood pressure, changes in tissue pressure, changes in tissue temperature, changes in blood temperature, and changes in tissue metabolism.

According to certain embodiments of the invention a method for determining perfusion in living tissue includes the steps of (1) establishing baseline tissue criteria by determining an unperturbed temperature of the tissue, causing the temperature of the tissue to change from a first unperturbed temperature to a second temperature different from said first temperature for a time period, and determining a value or values for one or more thermal properties of the tissue during the time period; (2) calculating a perfusion value for the tissue during the time period using said thermal property value or values, and (3) evaluating one or more physiological and artifactual conditions to determine if previously established baseline criteria are materially affected by said conditions. If previously established baseline criteria are materially affected by changed conditions, (4) the first step is repeated to establish new values for baseline thermal properties. The thermal properties for which a value or values are determined may include either or both of thermal conductivity and thermal diffusivity.

Certain embodiments of a method for measuring perfusion in tissue comprise the steps of (1) establishing a baseline criteria for tissue conditions, comprising the steps of: (A) determining an unperturbed temperature of the tissue, (B) causing the temperature of said tissue to change from a first unperturbed temperature to a second temperature different from said first temperature during a time period the initial portion of which is affected strongly by conductive factors and a second portion of which is affected strongly by convective factors, (C) calculating an intrinsic thermal conductivity and a diffusivity of said tissue during a first selected portion of said time period, (2) obtaining measurements of perfusion of the tissue comprising the steps of: (A) calculating a perfusion of said tissue at a second selected portion of said time period using said calculated intrinsic thermal conductivity and diffusivity, (B) re-calculating the intrinsic thermal conductivity and diffusivity of said tissue during said first selected portion of said time period using said calculated perfusion, (C) re-calculating the perfusion of said tissue at said second selected portion of said time period using said recalculated intrinsic thermal conductivity and diffusivity, and (D) repeating steps 2(B) and 2(C) until the re-calculated intrinsic thermal conductivity and diffusivity and the re-calculated perfusion each converge to a substantially non-changing value; (3) determining need for new baseline criteria comprising evaluating physiological conditions that may affect baseline temperature, conductivity and/or diffusivity values.

In certain embodiments step (3) further comprises the step of evaluating measurement artifact conditions that may affect baseline temperature, conductivity and/or diffusivity values. Other embodiments further comprise a step (4) when new baseline criteria are indicated by step (3) for permitting the temperature of the tissue to relax to an unperturbed state and then repeating step (1). In certain other embodiments step (1)(B) includes: activating said temperature changing means when immersed in said tissue to change the temperature of said tissue. In still other embodiments step (1)(B) includes: immersing a cooling means in said tissue; and applying power to said cooling means to cool said tissue from said first unperturbed temperature. The intrinsic thermal conductivity and diffusivity of step (1)(C) are calculated at the first selected portion of said time period when convective factors dominate and step (2)(A) is calculated at the second selected portion of said time period when conductive factors dominate.

In certain embodiments step (1)(B) includes: applying power to said heating means while in contact with said tissue to heat said tissue from said first unperturbed temperature to said second temperature. In other embodiments the heating means has a substantially spherical configuration and is of a type referenced in the previously mentioned U.S. Pat. Nos. 4,059,981 and 5,035,514. Said intrinsic thermal conductivity and diffusivity are calculated and recalculated in steps (1)(C) and (2)(B) and the perfusion is calculated and recalculated in steps (2)(A) and (2)(C) using the following equation:

$$P(t) = \frac{4\pi a k_m \Delta T}{\frac{1}{5\gamma} + \frac{1}{1+\lambda a}} \left[ 1 + \frac{\frac{a}{\sqrt{\pi \alpha_m}} f(t)}{\frac{1-\lambda^2 a^2}{5\gamma} + 1 + \lambda a} \right] \quad \text{(i)}$$

$$V_b(t) = \Delta T$$

$$P(t) = 0$$

$$\frac{V_b(t)}{\Delta T} = \frac{a/\sqrt{\pi \alpha_m}}{\frac{1-\lambda^2 a^2}{5\gamma} + 1 - \lambda a} \left[ \{f(t-t_{heat}) - f(t)\} + \frac{a/\sqrt{\pi \alpha_m}}{\frac{1-\lambda^2 a^2}{5\gamma} + 1 + \lambda a} \frac{\sqrt{t_{heat}} e^{-\lambda^2 \alpha m'}}{t\sqrt{t-t_{heat}}} \right] \quad \text{(ii)}$$

wherein P(t) is the power applied, a is the radius of the spherical heating means, $k_m$ and $\alpha_m$ are, respectively, the intrinsic thermal conductivity and thermal diffusivity of said tissue, $\gamma$ is the ratio $k_b/k_m$, $k_b$ is the intrinsic thermal conductivity of the spherical heating means, $\lambda$ is equal to $\sqrt{wc_m/k_m}$, where w is perfusion and $c_m$, is the specific heat of the perfusate, $V_b$ is the bead mean volumetric temperature during cooling, $\Delta T$ is the volume averaged constant temperature change during the heating phase, $t_{heat}$ is the length of time for which heating is applied and f(t) represents the temporal form of the transient power applied to said heating means as a function of time.

Other variations, include but are not limited to, where said heating means has a substantially spherical configuration and said intrinsic thermal conductivity and diffusivity are calculated and recalculated in steps (1)(C) and (2)(B) and the perfusion is calculated and recalculated in steps (2)(A) and (2)(C) using the following equation:

$$P = P_0$$

and $$V_b(t) = \frac{P_o}{4\pi a k_a} \left[ \frac{1}{5\gamma} + \frac{1}{1+\lambda a} - \frac{a/\sqrt{\pi \alpha_m}}{1-\lambda^2 a^2} f(t) \right] \quad \text{(iii)}$$

$$P = 0$$

$$V_b(t) = \frac{P_o}{4\pi a k_a \sqrt{\pi \alpha_m}} \frac{1}{1-\lambda^2 a^2} [f(t-t_{heat}) - f(t)] \quad \text{(iv)}$$

wherein $P_o$ is the constant power applied during the heating phase, a is the radius of the spherical heating means, $k_m$ and $\alpha_m$ are, respectively, the intrinsic thermal conductivity and thermal diffusivity of said tissue, $\gamma$ is the ratio $k_b/k_m$, $k_b$ is the intrinsic thermal conductivity of the spherical heating means, $\lambda$ is equal to $\sqrt{wc_m/k_m}$, where w is perfusion and $c_f$ is the specific heat of the perfusate, $V_b$ is the bead mean volumetric temperature during a cool-down period, $t_{heat}$ is the length of time for which heating is applicated and f(t) represents the temporal form of the transient power applied to said heating means as a function of time.

In accordance with certain embodiments, a method for determining thermal properties of a medium comprises the steps of (A) establishing reference parameters for measuring, comprising determining unperturbed temperature of medium; (B) obtaining measurements of medium comprising the steps of: (1) causing the temperature of said medium to change from a first unperturbed temperature to a second temperature different from said first temperature during an overall time period, (2) calculating effective thermal conductivity and diffusivity values of said medium during a plurality of time periods within said overall time period, (3) extrapolating the effective thermal conductivity and diffusivity values calculated in step (2) to the thermal conductivity and diffusivity values at a selected time $t_o$ when the temperature of said medium is first caused to change so as to determine the extrapolated values of the intrinsic thermal conductivity and diffusivity of said medium, (4) calculating a perfusion of said medium during a selected time period of said overall time period using said extrapolated intrinsic thermal conductivity and diffusivity, (5) recalculating the effective thermal conductivity and diffusivity values of said medium during said plurality of time periods; using said calculated perfusion, (6) re-extrapolating the thermal conductivity and diffusivity values recalculated in step (5) to the intrinsic thermal conductivity and diffusivity values at said selected time $t_o$, (7) recalculating the perfusion of said medium during said selected time period using the intrinsic thermal conductivity and diffusivity values reextrapolated in step (6); and (8) repeating steps (5) through (7) until the recalculated intrinsic thermal conductivity and diffusivity values and the recalculated perfusion value converge to substantially non-changing values; (C) determining the need for new reference parameters for medium.

In certain preferred embodiments the temperature change produced in said medium is constant and further wherein in steps (2) and (5) the thermal conductivity and diffusivity are calculated in accordance with the following equation:

$$P(t) = \frac{4\pi a k_a \Delta T}{\frac{1}{5\gamma} + \frac{1}{1+\lambda a}} \left[ 1 + \frac{\frac{a}{\sqrt{\pi \alpha_a}} f(t)}{\frac{1-\lambda^2 a^2}{5\gamma} + 1 + \lambda a} \right]$$

In other embodiments the temperature change produced in said medium is constant and further wherein in steps (4) and (7) the perfusion is calculated in accordance with the following equation:

$$P(t) = \frac{4\pi a k_a \Delta T}{\frac{1}{5\gamma} + \frac{1}{1+\lambda a}} \left[ 1 + \frac{\frac{a}{\sqrt{\pi \alpha_a}} f(t)}{\frac{1-\lambda^2 a^2}{5\gamma} + 1 + \lambda a} \right]$$

In still other embodiments the temperature change produced in said medium is constant and further wherein in step (4) and (7) the perfusion is calculated in accordance with the following equation, for a time period which is subsequent to the deactivation of the temperature changing means:

$$\frac{V_b(t)}{\Delta T} = \frac{a/\sqrt{\pi \alpha_m}}{\frac{1-\lambda^2 a^2}{5\gamma} + 1 - \lambda a} \left[ \frac{\{f(t-t_{heat}) - f(t)\} +}{\frac{a/\sqrt{\pi \alpha_m}}{5\gamma} + 1 + \lambda a} \frac{\sqrt{t_{heat}}}{t\sqrt{t-t_{heat}}} e^{-\lambda 2\alpha m'} \right]$$

Other embodiments have the temperature change in said medium produced by activating a power source so as to produce a change in power which is constant and further wherein in steps (2) and (5) the thermal conductivity and diffusivity are calculated in accordance with the following equation:

$$V_b(t) = \frac{P_o}{4\pi a k_a} \left[ \frac{1}{5\gamma} + \frac{1}{1+\lambda a} - \frac{a/\sqrt{\pi \alpha_m}}{1-\lambda^2 a^2} f(t) \right]$$

The temperature change in said medium may also be produced by activating a power source so as to produce a change in power which is constant and further wherein in steps (4) and (7) the perfusion is calculated in accordance with the following equation:

$$V_b(t) = \frac{P_o}{4\pi a k_a} \left[ \frac{1}{5\gamma} + \frac{1}{1+\lambda a} - \frac{a/\sqrt{\pi \alpha_m}}{1-\lambda^2 a^2} f(t) \right]$$

Other embodiments have the temperature change in said medium produced by activating a power source so as to produce a change in power which is constant and further wherein in steps (4) and (7) the perfusion is calculated in accordance with the following equation, for a time period which is subsequent to the deactivation of the power source:

$$V_b(t) = \frac{P_o}{4\pi a k_a \sqrt{\pi \alpha_m}} \frac{1}{1-\lambda^2 a^2} [f(t-t_{heat}) - f(t)]$$

FIG. 2 depicts a block diagram of showing the basic steps of the above mentioned methods.

Figure 5:
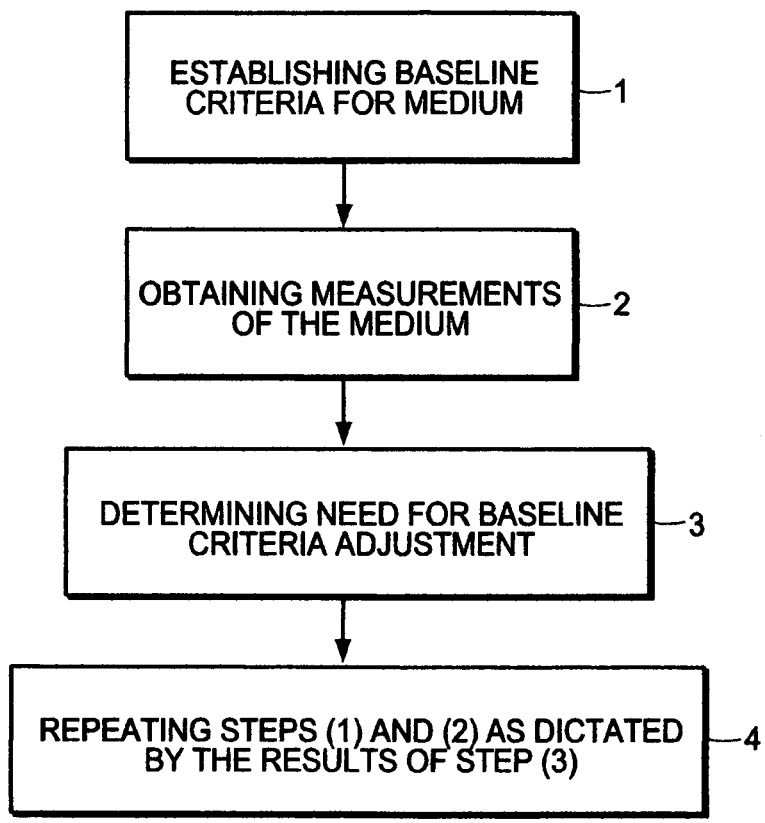
FIG. 5 is a high-level general block diagram of a method for determining properties of a medium.

In the embodiment illustrated by FIG. 5, step (1) consists of determining baseline conditions in the medium and establishing baseline criteria based thereon. This step can involve numerous steps but the basic purpose is to establish a reference for the medium that all following measurements will be compared against. The criteria can come from the probe of the measuring device, can be user inputted, or obtained from other instrumentation. This step may also include the step of calibrating the instrumentation used; that is, establishing baseline criteria for the instrumentation.

Step (2) comprises of obtaining measurements of the medium, for example, live tissue. In a preferred embodiment this comprises raising the temperature of the medium and monitoring the time, and power required to raise and then maintain the new temperature. In some cases this step may also include ceasing to heat the medium and monitoring the cool down rate. From this process properties of the medium such as thermal conductivity and rate of flow can be calculated. These measurements and calculations may be performed multiple times.

Step (3) comprises determining if new baseline criteria need to be established. In a preferred embodiment the baseline conditions on which baseline criteria are based are monitored thru-out the method. If there is a change indicating that conditions of the medium or other conditions on which baseline criteria are based have changed, calculations and measurements based on the original baseline conditions may no longer be valid. Therefore it may be necessary to obtain a new baseline. In certain embodiments step (3) comprises the steps of: comparing measurements taken and calculated to established baseline criteria to existing measurements and determining if there has been a change in conditions. In other embodiments step (3) comprises the steps of comparing measurements received from other instrumentation to baseline criteria, and determining if there has been a change in conditions.

In certain embodiments the methods have an additional step (4) consisting of repeating the process again if new baseline criteria are required. This includes establishing new baseline criteria and obtaining new measurements based on the new baseline criteria.

In accordance with certain embodiments, a method for determining properties of a medium comprises the steps of determining baseline conditions and establishing baseline criteria for the medium; inducing a temperature change in the medium during a predetermined interval; calculating at least one selected intrinsic thermal property of said medium using data obtained at a first time period; calculating separately a perfusion rate of said medium using data obtained at a second time period and said at least one calculated intrinsic thermal property, the effects of the perfusion of said medium at said second time period being greater than the effects of the perfusion of said medium at said first time period; and determining the need for new baseline criteria for the medium. The invention may further comprise repeating the previous steps to obtain another perfusion rate of the medium when need for a new baseline is indicated.

In accordance with certain other embodiments, a method for determining properties of a medium with automatic recalibration comprises the steps: 1) measuring the temperature of the medium at a first and second location; 2) determining if the temperatures at the first and second location are stable, wherein if the temperature at either the first or second location are not stable then repeating step 1; 3) raising the temperature of the medium at the second location a predetermined amount; 4) measuring the temperature at the first location and calculating the power required to raise the temperature at the second location; 5) repeating step 4 for a set period of time; 6) calculating the intrinsic thermal conductivity of the medium; 7) calculating the rate of flow of the medium; 8) determining if the temperature of the medium at the first location is stable, wherein if the temperature at the first location is not stable, then repeating step 1; 9) determining if the change in power over time is less than an established maximum value, wherein if the change in power over time is not less than the established maximum, then repeating step 1; 10) determining if the total time the measurements have been taken over is less than an established maximum, wherein if the total is not less than the established maximum, then repeating step 1; 11) repeating step 4.

In accordance with one embodiment, in a method for determining properties of a medium comprising the steps of (1) causing the temperature of said medium to change from a first unperturbed temperature to a second temperature different from said first temperature during a first time period; (2) causing the temperature of said medium to relax to a final unperturbed temperature during a second time period; (3) calculating an intrinsic thermal conductivity and a diffusivity of said medium during a first selected portion of said first and second time periods; (4) calculating a perfusion of said medium at, at least a second selected portion of said first and second time periods, using said calculated intrinsic thermal conductivity and diffusivity; (5) recalculating the intrinsic thermal conductivity and diffusivity of said medium during said first selected portion of said first and second time periods using said calculated perfusion; (6) recalculating the perfusion of said medium at least at said second selected portion of said first and second time periods using said recalculated intrinsic thermal conductivity and diffusivity; and (7) repeating steps (5) and (6) until the recalculated intrinsic thermal conductivity and diffusivity and the recalculated perfusion each converge to a substantially non-changing value; an improvement comprises the steps of: (a) prior to step (1), establishing baseline criteria that correspond to properties of the medium; and (b) periodically determining the need for and establishing new baseline criteria.

In accordance with certain embodiments, represented by the block diagram of FIG. 5, a method for determining properties of a medium comprises the steps of: (1) establishing baseline criteria for medium conditions or properties, comprising: determining the thermal conductivity of a heating means, said heating means having a predetermined resistance versus temperature relationship, and determining the reference temperature of said medium when said heating means is immersed in said medium and said medium is unheated; (2) obtaining measurements of medium comprising the steps of: applying power to said heating means sufficiently rapidly to heat said means to a volume mean temperature above said reference temperature so that the power necessary to maintain said volume mean temperature varies as a function of time, determining the time varying relationship between the power required to maintain said heating means at said volume mean temperature after said temperature has been reached and the time during which said power is being applied thereto, determining the temperature difference between said volume mean temperature and said reference temperature and determining the resistance of said heating means at said volume mean temperature, determining the thermal conductivity of said medium as a function of said temperature difference, of the resistance of said heating means at said volume mean temperature, of said applied power in accordance with said time varying power and time relationship, of said predetermined thermal conductivity of said heating means, and of at least one characteristic dimension of said heating means in accordance with a thermal model of said heating means and said medium in which it is immersed wherein said heating means is treated as a distributed thermal mass and wherein heat conduction occurs in a coupled thermal system which comprises both the heating means and the adjacent region of said medium which surrounds said heating means; and (3) determining need for new baseline criteria comprising evaluating physiological conditions that may materially affect the baseline criteria. Examples of physiological conditions include but are not limited to tissue and vascular damage, tissue edema, tissue scar formation, influence of a large vessel, change in vascular status such as blood volume, vasodilation, and vasoconstriction; changes in perfusion, changes in blood pressure, changes in tissue pressure, changes in tissue temperature, changes in blood temperature, and changes in tissue metabolism.

In certain preferred embodiments step (3) further comprises the step of evaluating measurement artifact conditions that may materially affect the baseline criteria. Examples of measurement artifact conditions include but are not limited to sensor motion relative to the tissue, excessive sensor such as tissue contact force or capillary collapse, insufficient sensor-tissue contact force such as artifactual transduction of perfusion, sensor cross-talk, ambient temperature changes, electrical interference, instrumentation drift, automatically perform a recalibration, probe recalibration, and instrumentation recalibration. In other embodiments the method further comprises step (4): repeating steps (1) and (2) when indicated by step (3).

In a certain preferred embodiment, in step (1), said reference temperature is determined over a relatively short time period over which it remains substantially constant and step (2) further including the steps of: maintaining said volume mean temperature at a fixed, predetermined value above said reference temperature, said time varying power and time relationship being determined in terms of the relationship between the square of the voltage applied to said heating means and the inverse square root of the time during which said voltage is being applied; determining a first characteristic $\Gamma$ of said relationship representing the value of the power per unit volume generated by the heating means at a time t effectively equivalent to an infinite time period following the application of said power to said heating means; and further wherein said thermal conductivity of said medium is determined in accordance with the expression:

$$k = \frac{5}{\frac{15\Delta T}{\Gamma \bar{a}^2} - \frac{1.0}{k_b}}$$

where k is the thermal conductivity of said medium, $\Delta T$ is the said fixed volume mean temperature difference, $\bar{a}$ is the radius of a spherical heating means having a volume equivalent to the actual volume of said heating means, and $k_b$ is said predetermined thermal conductivity of said heating means.

In still other embodiments, in step (1), the step of determining said reference temperature includes the steps of: measuring the voltage at said heating means in its unheated state; determining the current through said heating means in its unheated state; determining the resistance of said heating means in its unheated state; and determining said reference temperature in accordance with the said predetermined resistance versus temperature relationship of said heating means.

In another embodiment according to step (2), the step of maintaining said volume mean temperature at said fixed value further includes the steps of: preselecting a fixed value for said temperature difference; determining said volume mean temperature from said reference temperature and said preselected fixed temperature difference; determining the resistance of said heating means at said volume mean temperature in accordance with said predetermined resistance versus temperature relationship; and maintaining the resistance of said heating means at a substantially constant value equal to said determined resistance whereby said volume mean temperature remains at a substantially constant value.

In another embodiment wherein the time varying relationship between the square of the voltage $V_h^2$ and the inverse square root of the time $t^{-1/2}$ is a substantially linear relationship of the form $V_h^2(t)=m_1+m_2t^{-1/2}$; and further wherein said first characteristic $\Gamma$ is determined in accordance with the expression:

$$\Gamma = \frac{m_1}{R_h \frac{4}{3}\pi(\overline{a})^3}$$

Other embodiments further include the steps of: predetermining the thermal diffusivity of said heating means; determining a second characteristic $\beta$ representing the slope of the time varying relationship between the square of the voltage $v_h^2$ and the inverse square root of the time $t^{-1/2}$ at a time relatively shortly after the time at which said power is applied; predetermining the non-dimensional relationship between the expression $\beta\sqrt{\alpha_b}/\Gamma\overline{a}$ wherein $\alpha_b$ is the predetermined thermal diffusivity of said heating means; the expression $k_m/k_b$, wherein $k_m$ is the thermal conductivity of said medium with no fluid flowing therein; and the expression $\alpha_b/\alpha_m$ where $\alpha_m$ is thermal diffusivity of any medium which is to be determined; determining the actual value of $\beta\sqrt{\alpha_b}/\Gamma\overline{a}$ and $k_m/k_b$ at said volume mean temperature and further determining the value of $\alpha_b/\alpha_m$ in accordance with said predetermined non-dimensional relationship; and determining the thermal diffusivity $\alpha_m$ of said medium in accordance with the determined value of $\alpha_b/\alpha_m$.

In certain preferred embodiments time varying relationship between the square of the voltage $V_h^2$ and the inverse square root of time $t^{-1/2}$ is a substantially linear relationship of the form $V_h^2(t)=m_1+m_2t^{-1/2}$; and further wherein said first characteristic $\Gamma$ is determined in accordance with the expression:

$$\Gamma = \frac{m_1}{R_h \frac{4}{3}\pi(\overline{a})^3};$$

and
said second characteristic $\beta$ is determined in accordance with the expression:

$$\beta = \frac{m_2}{R_h \frac{4}{3}\pi(\overline{a})^3}$$

In other embodiments the reference temperature varies with time over a relatively long time period and further including the steps of: determining said reference temperature value over said time period; maintaining said volume mean temperature at a fixed, predetermined value, said fixed value being greater than said reference temperature over said time period; determining the time-varying temperature difference between said fixed volume mean temperature and said time-varying reference temperature; determining the fixed value of the resistance of said heating means at said volume mean temperature; and determining the thermal conductivity of said medium over said time period in accordance with the expression:

$$k(t) = \frac{5}{\frac{\Delta T(t)R_h 20\pi\overline{a}}{V_h^2(t)} - \frac{1.0}{k_b}}$$

where $k(t)$ is the thermal conductivity of said medium, $\Delta T$ is said temperature difference, $R_h$ is the said fixed resistance of said heating means at said volume mean temperature, a is the radius of a spherical heating means having a volume equivalent to the actual volume of said heating means, $V_h(t)$ is the voltage at said heating means where said power is applied, and $k_b$ is said predetermined thermal conductivity of said heating means.

In some embodiments the step of determining said reference temperature includes the steps of: immersing a temperature sensing means in said medium at a region sufficiently remote from the immersed heating means so that the temperature sensed by said sensing element is not materially affected by the raised temperature of said heating means, said sensing means having a predetermined resistance versus temperature relationship; determining over said time period the voltage at said sensing means and the current through said sensing means; determining the reference temperature sensed by said sensing means over said time period in accordance with the said predetermined resistance versus temperature relationship thereof.

In another embodiment, the steps thereof are first performed when no fluid is flowing in said medium to determine the intrinsic thermal conductivity $k_m$ of said medium and said steps are further performed over said time period when a fluid having a predetermined heat capacity is flowing in said medium to determine the effective thermal conductivity $k_{eff}(t)$ of said medium; and further including the steps of: predetermining the heat capacity $C_b$ of said fluid; determining the ratio of $k_{eff}(t)$ $k_m$ over said time period; and determining the rate of flow $\omega(t)$ of said fluid in said medium in accordance with the expression:

$$\omega(t) = \left(\frac{k_{eff}(t)}{k_m} - 1\right)^2 \frac{k_m}{C_b(\overline{a})^2}$$

where $\omega(t)$ is measured in terms of the mass of fluid per unit volume of the medium per unit time.

In another embodiment the reference temperature varies with time over a relatively long time period and further including the steps of determining said reference temperature over said time period; determining the said volume mean temperature over said time period as a function of said reference temperature and a preselected fixed value of said temperature difference; maintaining the resistance of said heating means over said time period at a value such as to maintain the temperature difference between said volume mean temperature and said reference temperature at said preselected fixed value, said resistance varying as a function of time; determining the thermal conductivity $k(t)$ of said medium over said time period in accordance with the expression:

$$k(t) = \frac{5}{\frac{\Delta T(t)R_h 20\pi\overline{a}}{V_h^2(t)} - \frac{1.0}{k_b}}$$

where $\Delta T$ is said temperature difference, $R_h(t)$ is said resistance of said heating means at said volume mean temperature, ā is the radius of a spherical heating means having a volume equivalent to the actual volume of said heating means, $V_h(t)$ is the voltage at said heating means when said power is applied and $k_b$ is the predetermined thermal conductivity of said heating means.

In another embodiment, the step of determining said reference temperature includes the steps of: immersing a temperature sensing means in said medium at a region sufficiently remote from the immersed heating means so that the temperature sensed by said sensing element is not materially affected by the raised temperature of said heating means (referred to as sensor cross-talk), said sensing means having a predetermined resistance versus temperature relationship; determining over said time period the voltage at said sensing means and the current through said sensing means; determining the reference temperature sensed by said sensing means over said time period in accordance with the said predetermined resistance versus temperature relationship thereof.

In still other embodiments the steps thereof are first performed when no fluid is flowing in said medium to determine the intrinsic thermal conductivity $k_m$ of said medium and said steps are further performed over said time period when a fluid having a predetermined heat capacity is flowing in said medium to determine the effective thermal conductivity $k_{eff}(t)$ of said medium; and further including the steps of: predetermining the heat capacity $C_b$ of said fluid; determining the ratio of $k_{eff}(t)/k_m$ over said time period; and determining the rate of flow $\omega(t)$ of said fluid in said medium in accordance with the expression:

$$\omega(t) = \left(\frac{k_{eff}(t)}{k_m} - 1\right)^2 \frac{k_m}{C_b(\bar{a})^2}$$

where $\omega(t)$ is measured in terms of the mass of the fluid per unit volume of the medium per unit time.

In another embodiment, the reference temperature varies with time over a relatively long time period and further including the steps of: immersing a temperature sensing means in said medium at a region sufficiently remote from the immersed heating means so that the temperature sensed by said sensing element is not affected by the raised temperature of said heating means, said sensing means having a predetermined resistance versus temperature relationship; determining the resistance of said sensing means over said time period; determining the reference temperature of said sensing means over said time period; determining the desired resistance of said heating means over said time period as a function of the resistance of said sensing means and of a preselected fixed value of the resistance difference between the resistances of said sensing means and said heating means; maintaining the resistance of said heating means at said desired resistance value over said time period so that said resistance difference remains at said preselected fixed value, the resistance of said heating means varying as a function of time; determining the mean temperature of said heating means over said time period at the said desired resistance value of said heating means, said mean temperature varying as a function of time; determining the temperature difference between said mean temperature and said reference temperature over said time period, said temperature difference varying as a function of time; determining the thermal conductivity k(t) of said medium over said time period in accordance with the expression:

$$k(t) = \frac{5}{\frac{\Delta T(t) R_h 20\pi \bar{a}}{V_h^2(t)} - \frac{1.0}{k_b}}$$

where $\Delta T(t)$ is said temperature difference, $R_h(t)$ is said resistance of said heating means at said mean temperature, a is the radius of a spherical heating means having a volume equivalent to the actual volume of said heating means, $V_h(t)$ is the voltage at said heating means when said power is applied and $k_b$ is the predetermined thermal conductivity of said heating means.

In another embodiment, the step of determining said reference temperature includes the steps of immersing a temperature sensing means in said medium at a region sufficiently remote from the immersed heating means to that the temperature sensed by said sensing element is not affected by the raised temperature of said heating means (i.e.: no sensor cross-talk), said sensing means having a predetermined resistance versus temperature relationship; determining over said time period the voltage at said sensing means and the current through said sensing means; determining the reference temperature sensed by said sensing means over said time period in accordance with the said predetermined resistance versus temperature relationship thereof.

In other embodiments, the steps thereof are first performed when no fluid is flowing in said medium to determine the intrinsic thermal conductivity $k_m$ of said medium and said steps are further performed over said time period when a fluid having a predetermined heat capacity is flowing in said medium to determine the effective thermal conductivity $k_{eff}(t)$ of said medium; and further including the steps of predetermining the heat capacity $C_b$ of said fluid; determining the ratio of $k_{eff}(t)/k_m$ over said time period; and determining the rate of flow of said fluid in said medium in accordance with the expression:

$$\omega(t) = \left(\frac{k_{eff}(t)}{k_m} - 1\right)^2 \frac{k_m}{C_b(\bar{a})^2}$$

where $\omega(t)$ is measured in terms of the mass of the fluid per unit volume of medium per unit time.

Figure 6:
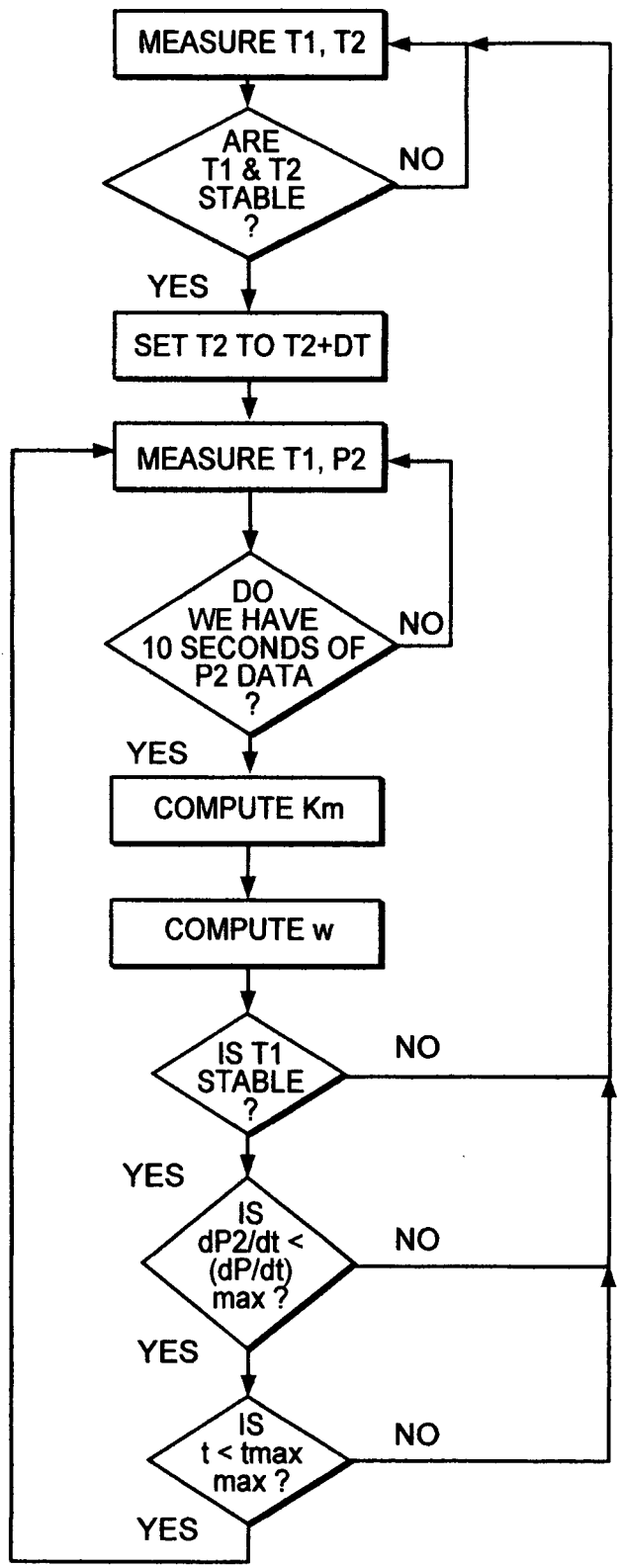
FIG. 6 is detailed block diagram of a method for determining properties of a medium.

A more specific preferred embodiment can be seen in the block diagram of FIG. 6 wherein the method comprises the steps of: 1) measuring T1 and T2, the temperatures at a first and second location; 2) determining if T1 and T2, the temperatures at the first and second locations are stable; 3) if T1 and T2 are not stable, then repeating step 1; 4) if T1 and T2 are stable, then setting T2 to a different temperature, T2+DT; 5) measuring T1 and calculating P2, the power required to change the temperature at the second location; 6) determining if P2 data has been acquired for a selected time period (i.e.: 10 seconds); 7) if 10 seconds of P2 data not acquired, then repeat step 5; 8) if 10 seconds of P2 data has been acquired, then calculating intrinsic thermal conductivity of the medium, Km; 9) calculating perfusion, w; 10) determining if T1 is stable; 11) if T1 is not stable, then repeating step 1; 12) if T1 is stable, then determining if dP2/dt is less than dP/dt(max); 13) if dP2/dt is not less than dP/dt(max), then repeating step 1; 14) if dP2/dt is less than dP/dt(max), then determining if time, t, is less than established maximum time, t(max); 15) if t is not less than t(max), then repeating step 1; 16) if t is less than t(max), then repeating step 5.

In another embodiment, a method for determining properties of a medium comprises the steps of: (1) establishing baseline criteria corresponding to baseline conditions of the medium, comprising: determining the thermal conductivity of a heating means as a function of temperature, said heating means having a predetermined resistance versus temperature relationship; contacting said medium with said heating means; and determining the reference temperature of said medium when said medium is unheated; (2) obtaining measurements of medium comprising the steps of: applying power to said heating means sufficiently rapidly to heat said means to a temperature above said reference temperature so that the power necessary to maintain said temperature varies as a function of time; determining the time varying power and time relationship between the power required to maintain said temperature and the time during which said power is applied to said heating means; determining the temperature difference between said temperature and said reference; determining the thermal conductivity of said medium as a function of said temperature difference, and of said applied power in accordance with said time varying power and time relationship; and (3) determining need for new baseline criteria comprising evaluating physiological conditions and/or artifact conditions changes in which may affect the baseline conditions of the medium.

Figure 7:
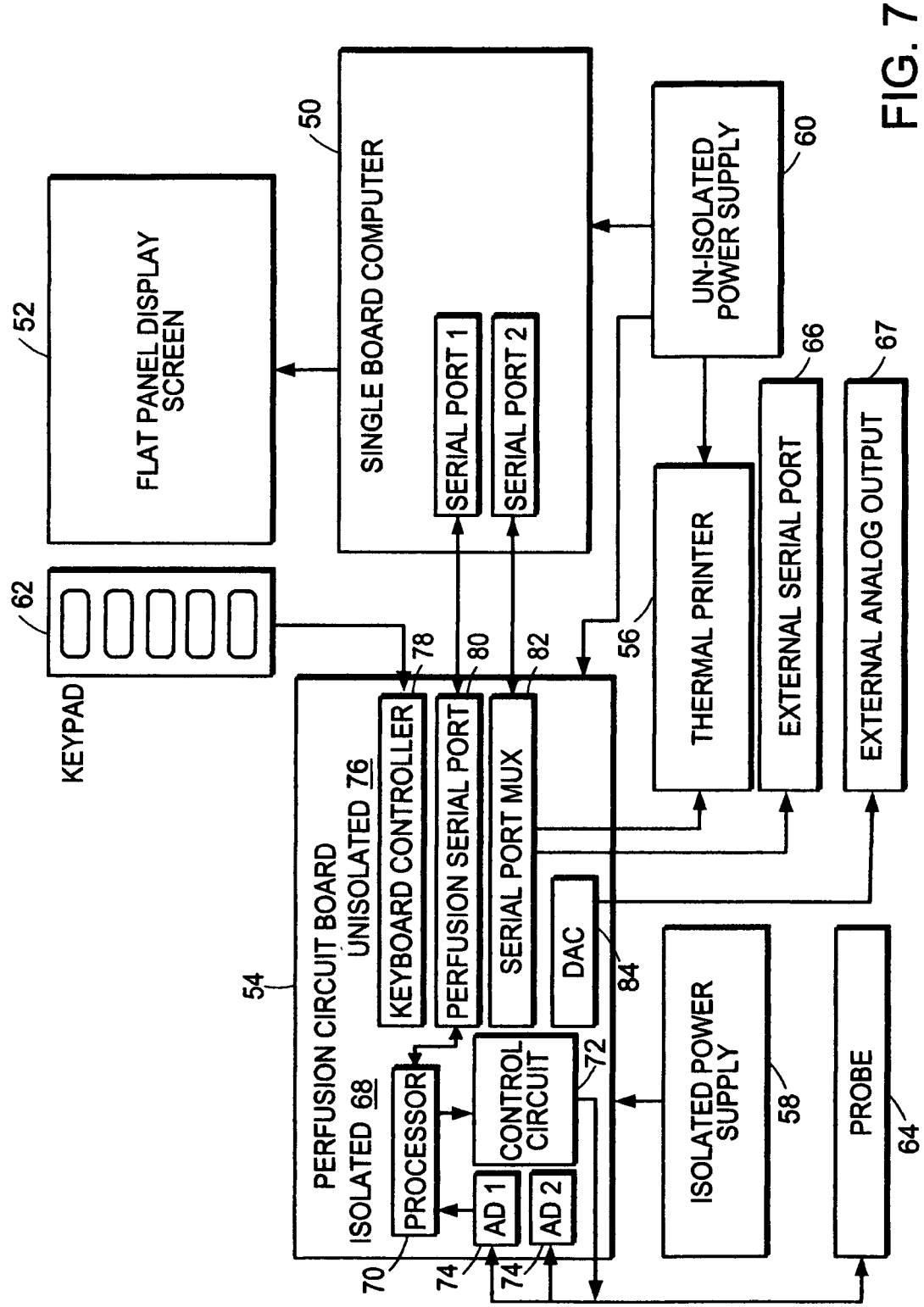
FIG. 7 is a block diagram of an apparatus for determining the properties of a medium.

Referring to FIG. 7, a method for determining properties of a medium with automatic recalibration comprises the steps of: 1) providing an apparatus for determining properties of a medium, comprising: a computer 50, a display 52 in electrical communication with the computer, a detector circuit 54 in electrical communication with the computer 50, a printer 56 in electrical communication with the detector circuit 54, a first power supply 58 in electrical communication with the detector circuit 54, a second power supply 60 in electrical communication with the computer 50, display 52, detector circuit 54, and printer 56; a keypad 62 in electrical communication with the detector circuit 54, and a probe 64 in electrical communication with the detector circuit 54; 2) inserting the probe into the medium; 3) having/operating the device perform the following steps: A) measuring the temperature of the medium at a first and second location; B) determining if the temperatures at the first and second location are stable, wherein if the temperature at either the first or second location are not stable then repeating step 1; C) raising the temperature of the medium at the second location a predetermined amount; D) measuring the temperature at the first location and calculating the perfusion at the second location; E) repeating step D for a set period of time; F) calculating the intrinsic thermal conductivity of the medium; G) calculating the rate of flow of the medium; H) determining if the temperature of the medium at the first location is stable, wherein if the temperature at the first location is not stable, then repeating step 1; I) determining if the rate of perfusion is less than an established maximum value, wherein if rate of perfusion is not less than the established maximum, then repeating step A; J) determining if the total time the measurements have been taken over is less than an established maximum, wherein if the total is not less than the established maximum, then repeating step A; K) repeating step D.

In accordance with further embodiments, an apparatus for determining physical characteristics of a medium is provided. One such apparatus comprises: temperature sensing means immersed in or contacting the medium for sensing the reference temperature of the medium when the medium is unheated; heating means immersed in the medium for heating the medium, the heating means having a predetermined thermal conductivity, a predetermined thermal diffusivity and a predetermined characteristic dimension; means for applying power to the heating means sufficiently rapidly to raise the temperature of the heating means to a volume mean temperature above the reference temperature so that the power necessary to maintain the volume mean temperature varies as a function of time; data processing means for determining the temperature difference between the volume mean temperature and the reference temperature, for determining the resistance of the heating means at the volume mean temperature and for determining the time varying relationship between the power required to maintain the heating means at the volume mean temperature after the temperature has been reached and the time during which the power is being applied thereto; the data processing means further being responsive to the temperature difference, the heating means resistance, the applied power in accordance with the time varying power and time relationship, the predetermined thermal conductivity of the heating means, a change in reference parameters, and the predetermined characteristic dimension of the heating means for determining the thermal conductivity of the medium in accordance with a thermal model of the heating means and the medium wherein the heating means is treated as a distributed thermal mass and wherein heat conduction occurs in a coupled thermal system which comprises both the heating means and the adjacent region of the medium which surrounds the heating means.

In certain embodiments the sensing means and the heating means comprises a single element capable of sensing the temperature of the medium and of heating the medium. An example of such a single element is a thermistor bead element, for example, of the type having characteristics referenced in above-mentioned U.S. Pat. Nos. 4,059,982 and 4,852,027. In other embodiments the apparatus further includes volume means for maintaining the mean temperature at a fixed, predetermined value above the reference temperature, the reference temperature being determined and the volume mean temperature being maintained over a relatively short time interval during which the reference temperature remains substantially constant whereby the temperature difference and the resistance of the heating means also remain substantially constant. Variations of such an embodiment further include: means for determining the time varying power and time relationship in terms of the relationship between the square of the voltage applied to the heating means and the inverse square root of the time during which the voltage is being applied; means for determining a first characteristic $\Gamma$ of the relationship representing the value of the power per unit volume generated by the heating means at a time t effectively equivalent to an infinite time period following the application of the power to the heating means; and means for determining the thermal conductivity of the medium in accordance with the expression:

$$k = \frac{5}{\frac{15\Delta T}{\Gamma a^2} - \frac{1.0}{k_b}}$$

where k is the thermal conductivity of the medium, $\Delta T$ is the mean temperature difference, a is the radius of a spherical heating means having a volume equivalent to the actual volume of the heating means and $k_b$ is the predetermined thermal conductivity of the heating means.

In still other embodiments, the time varying relationship between the square of the voltage $V_h^2$ and the inverse square root of the time t.sup.−½ is a substantially linear relationship of the form $V_h^2(t)=m_1+m_2t^{-1/2}$; and the first characteristic determining means includes means for determining the first characteristic $\Gamma$ in accordance with the expression:

$$\Gamma = \frac{m_1}{R_h \frac{4}{3}\pi(\bar{a})^3}$$

where $R_h$ is the resistance of the heating means at the volume mean temperature.

Variations of these embodiments further include: means for determining a second characteristic $\beta$ in accordance with the expression:

$$\beta = \frac{m_2}{R_h \frac{4}{3}\pi(\bar{a})^3}$$

memory storage means for storing the non-dimensional predeterminable relationship between the expression $\beta\sqrt{\alpha_b}/\Gamma\bar{a}$ wherein $\alpha_b$ is the predetermined thermal diffusivity of the heating means; the expression $k_m/k_b$, wherein $k_m$ is the thermal conductivity of the medium with no fluid flowing therein; and the expression $\alpha_b/\alpha_m$ is the thermal diffusivity of any medium which is to be determined; and means for determining the actual value of the expression $\beta\sqrt{\alpha_b}/\Gamma\bar{a}$ and $k_m/k_b$ and for determining the actual value of $\alpha_b/\alpha_m$ from the memory storage means; and means responsive to the value of $\alpha_b/\alpha_m$ for determining the thermal diffusivity $\alpha_m$ of the medium.

In other embodiments the sensing means and the heating means comprise: a first heating element immersed at a first region of the medium; and a second element immersed at a second region of the medium sufficiently remote from the first region as to be not affected or minimally affected by the heating of the first element. In certain embodiments the first and second elements are thermistor bead elements.

Other variations for use over a relatively long time period during which the reference temperature varies with time and wherein the second element determines the reference temperature over the time period; further include: means for maintaining the volume mean temperature and the resistance of the heating means at the volume mean temperature at fixed predetermined values over the time period during which the reference temperature varies whereby the temperature difference there between varies over the time period.

Variations of such embodiments have the data processing means determine the thermal conductivity of the medium over the time period in accordance with the expression:

$$k(t) = \frac{5}{\frac{\Delta T(t)R_h 20\pi\bar{a}}{V_h^2(t)} - \frac{1.0}{k_b}}$$

where $k(t)$ is the thermal conductivity, $\Delta T(t)$ is the temperature difference, $R_h$ is the resistance of the heating means at the mean temperature, $V_h(t)$ is the voltage at the heating means as power is applied thereto, $\bar{a}$ is the radius of a spherical heating means having a volume equivalent to the actual volume of the heating means and $k_b$ is the predetermined thermal conductivity of the heating means. The data processing system may also include means for determining the intrinsic thermal conductivity $k_m$ of the medium when no fluid is flowing therein; means for determining the effective thermal conductivity $k_{eff}(t)$ of the medium when a fluid having a predetermined heat capacity is flowing therein; means for determining the ratio of $k_{eff}(t)/k_m$ over the time period; and means for determining the rate of flow $\omega(t)$ of the fluid in the medium in accordance with the expression:

$$\omega(t) = \left(\frac{k_{eff}(t)}{k_m} - 1\right)^2 \frac{k_m}{C_b(\bar{a})^2}$$

where $C_b$ is the predetermined heat capacity.

Other embodiments for use over a relatively long time period during which the reference temperature varies with time wherein the second element determines the reference temperature over the time period; and may further include means for determining the volume mean temperature over the time period as a function of the reference temperature and a preselected fixed value of the temperature difference; means for maintaining the resistance of the first element over the time period at a value such as to maintain the temperature difference between the volume mean temperature and the reference temperature at the preselected fixed value, the resistance varying as a function of time; and means for determining the thermal conductivity of the medium over the time period in accordance with the expression:

$$k(t) = \frac{5}{\frac{\Delta T(t)R_h 20\pi\bar{a}}{V_h^2(t)} - \frac{1.0}{k_b}}$$

where $\Delta T$ is the temperature difference, $R_h(t)$ is the resistance of the heating means at the volume mean temperature, $\bar{a}$ is the radius of a spherical heating means having a volume equivalent to the actual volume of the first element, $V_h(t)$ is the voltage at the first element when power is applied thereto, and $k_b$ is the predetermined thermal conductivity of the first element. The data processing system may include means for determining the intrinsic thermal conductivity $k_m$ of the medium when no fluid is flowing therein; means for determining the effective thermal conductivity $k_{eff}(t)$ of the medium when a fluid having a predetermined heat capacity is flowing therein; means for determining the ratio of $k_{eff}(t)/k_m$ over the time period; and means for determining the rate of flow $\omega(t)$ of the fluid in the medium in accordance with the expression:

$$\omega(t) = \left(\frac{k_{eff}(t)}{k_m} - 1\right)^2 \frac{k_m}{C_b(\bar{a})^2}$$

where $C_b$ is the predetermined heat capacity.

Still other embodiments for use over a relatively long time period during which the reference temperature varies with time wherein the second element determines the reference temperature over the time period; further include means for determining the resistance of the second element over the time period; means for determining the desired resistance of the first element over the time period as a function of the resistance of the second element and of a preselected fixed value of the resistance difference between the resistances of the second and the first elements; means for maintaining the resistance of the first element at the desired resistance so that the resistance difference is maintained at the predetermined fixed value, the resistance of the first element varying as a function of time; means for determining the volume mean temperature of the first element over the time period at the desired resistance of the first element, the volume mean temperature varying as a function of time; means for determining the temperature difference between the volume mean temperature and the reference temperature over the time period, the temperature difference varying as a function of time; means for determining the thermal conductivity of the medium over the time period in accordance with the expression:

$$k(t) = \frac{5}{\frac{\Delta T(t) R_h 20\pi \bar{a}}{V_h^2(t)} - \frac{1.0}{k_b}}$$

where $\Delta T(t)$ is the temperature difference, $R_h(t)$ is the resistance of the heating means at the volume mean temperature, a is the radius, of a spherical heating means having a volume equivalent to the actual volume of the first element, $V_h(t)$ is the voltage at the first element when power is applied thereto, and $k_b$ is the predetermined thermal conductivity of the first element. The data processing system may include means for determining the intrinsic thermal conductivity $k_m$ of the medium when no fluid is flowing therein; means for determining the effective thermal conductivity $k_{eff}(t)$ of the medium when a fluid having a predetermined heat capacity is flowing therein; means for determining the ratio of $k_{eff}(t)/k_m$ over the time period; and means for determining the rate of flow $\omega(t)$ of the fluid in the medium in accordance with the expression:

$$\omega(t) = \left(\frac{k_{eff}(t)}{k_m} - 1\right)^2 \frac{k_m}{C_b(\bar{a})^2}$$

where $C_b$ is the predetermined heat capacity.

Referring again to FIG. 7, apparatus for determining thermal properties of living tissue in accordance with certain preferred embodiments will be described. An apparatus for determining properties of a medium, comprises: a computer 50; a display 52 in electrical communication with the computer 50; a detector circuit 54 in electrical communication with the computer 50; a printer 56 communicating with printed tape slot 63 (FIG. 1) and in electrical communication with the detector circuit 54; a first power supply 58 in electrical communication with the detector circuit 54; a second power supply 60 in electrical communication with the computer 50, display 52, detector circuit 54, and printer 56; a keypad 62 in electrical communication with the detector circuit 54; and a probe 64 in electrical communication with the detector circuit 54. In certain embodiments the apparatus further comprises an external serial port 66 in electrical communication with the detector circuit 54. In other embodiments the apparatus further comprises an external output. This output may be either digital or analog.

The computer 50 may be any number of suitable microprocessor types, which may include optional peripheral devices for input and output of data. The computer illustrated is a single board microprocessor. The preferred computer may also comprise a first and second serial port. The display 52 may be any number of types, for example, a flat panel display. The first power supply 58 is an isolated power supply and the second power supply 60 is an un-isolated power supply.

In a preferred embodiment, the probe 64 comprises first and second thermistors 106 and 176, respectively, (FIGS. 8 and 9) in communication with a control circuit 72. One example of thermistors that can be used with this embodiment are B35 and BR11 manufactured by Thermometrics, Inc. (Edison, N.J.). One example of a probe including such thermistors is shown in the above referenced U.S. Pat. No. 5,035,514. The detector circuit 54 comprises: an isolated component 68 comprising: a processor 70, the control circuit 72 in electrical communication with the processor 70, and at least one analog to digital converter 74; and an un-isolated component 76, in electrical communication with the processor 70 of the isolated component, comprising: a keyboard controller 78, a serial port 80, a serial port multiplexor 82, and a digital to analog converter 84.

Figure 8:
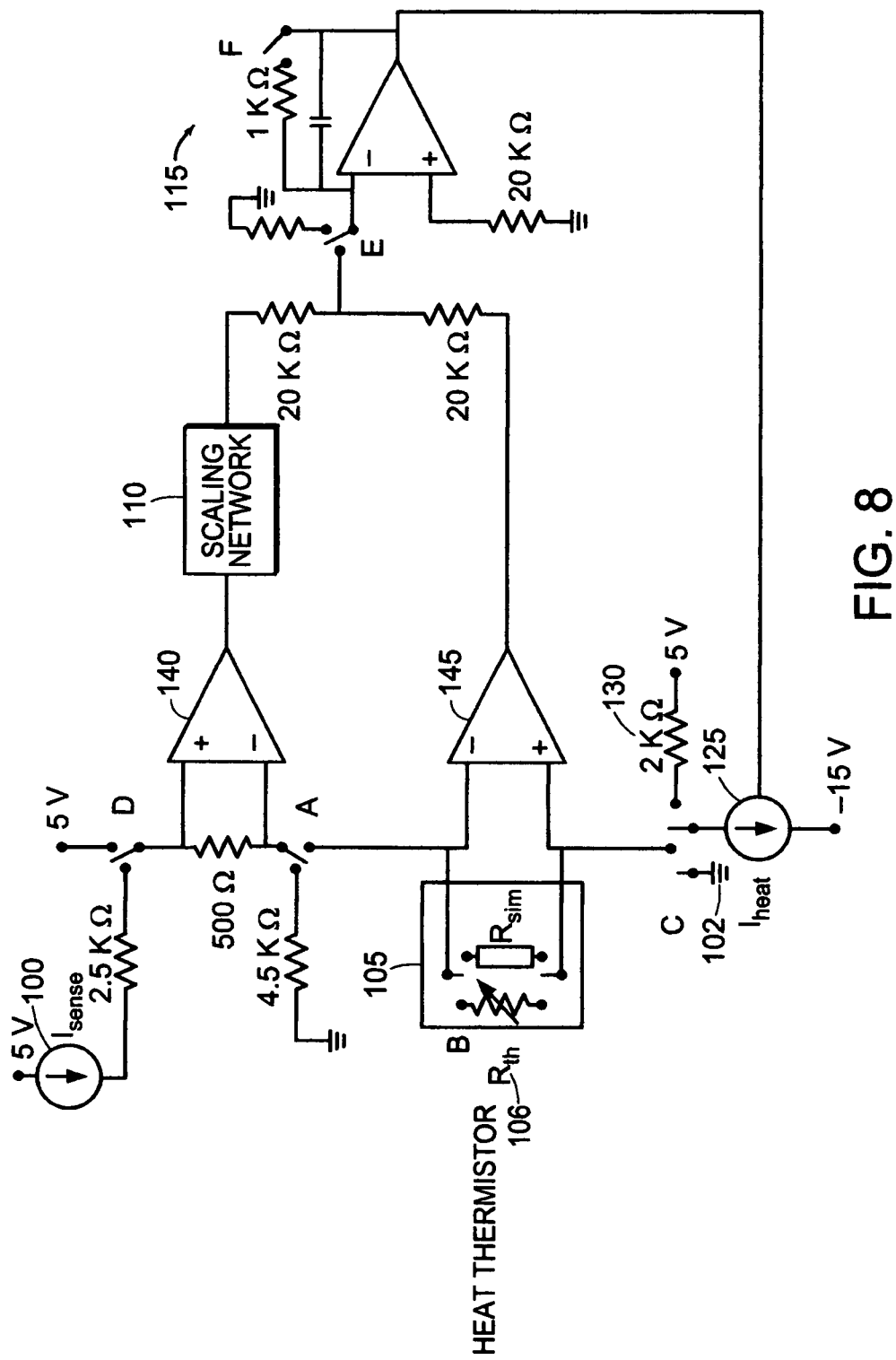
FIG. 8 is a simplified diagram of one embodiment of a circuit used in a control circuit.

The control circuit 72 will be referenced in connection with FIGS. 7 and 8. The control circuit serves to selectively measure temperature on or raise the temperature of the first or heat thermistor 106 of the probe 64.

A circuit for a Heat Thermistor Control Circuit 72 shown in FIG. 7, is also shown schematically in FIG. 8. The current source circuit 100 measures temperature using the thermistor 106 located in the probe 64. The circuitry of box 105 is the interface of the heat thermistor control circuit 72 with the thermistor 106. The functionality of the control circuit is controlled using switches A through F. The control circuit further comprises first 140 and second 145 op-amps in connection with a scaling network 110, an integrator 115, control resistor 150, and a current source 125. The probe 64 and thermistor 106 are connected to control circuit 72 through the probe interface 105, switch C and the connector 53 shown in FIG. 1.

In a passive temperature monitoring or sense mode, referring to FIG. 8, the thermistor 106 is connected to the sense current source 100 and to ground 102. Two precision resistors 150 and the 2.5 KOhm resistor shown between the current source and switch D are connected in series as well. The position of each switch for the sense (or unheated) mode is described in Table 1-1.

TABLE 1-1

Switch Positions for Sense Mode

| Switch | Position |
|---|---|
| A | right, connecting fixed resistor to thermistor |
| B | left, selecting thermistor |
| C | right, connecting thermistor to ground |
| D | left, connecting fixed resistor to current source |
| E | up, disconnecting feedback loop |
| F | closed, opamp as amplifier not integrator |

In the self-heating or heat mode, the resistor 150 and the thermistor 106 are connected to the current source 125 and, once the scaling network 110 is set for the desired level of amplification, the rest of the control loop is closed using the switches as described in Table 1-2.

TABLE 1-2

Switch Position for Heat Mode

| Switch | Position |
|---|---|
| A | right, connecting fixed resistor to thermistor |
| B | left, selecting thermistor |
| C | left, connecting thermistor to current sink |
| D | right, connecting fixed resistor to 5 V |

TABLE 1-2-continued

Switch Position for Heat Mode

| Switch | Position |
| --- | --- |
| E | down, closing feedback loop |
| F | open, opamp as integrator |

Element 103, unused in both the sense and heat modes as described, is a simulator for circuit testing purposes. Switch A is moved to the left position only for testing purposes.

Figure 9:
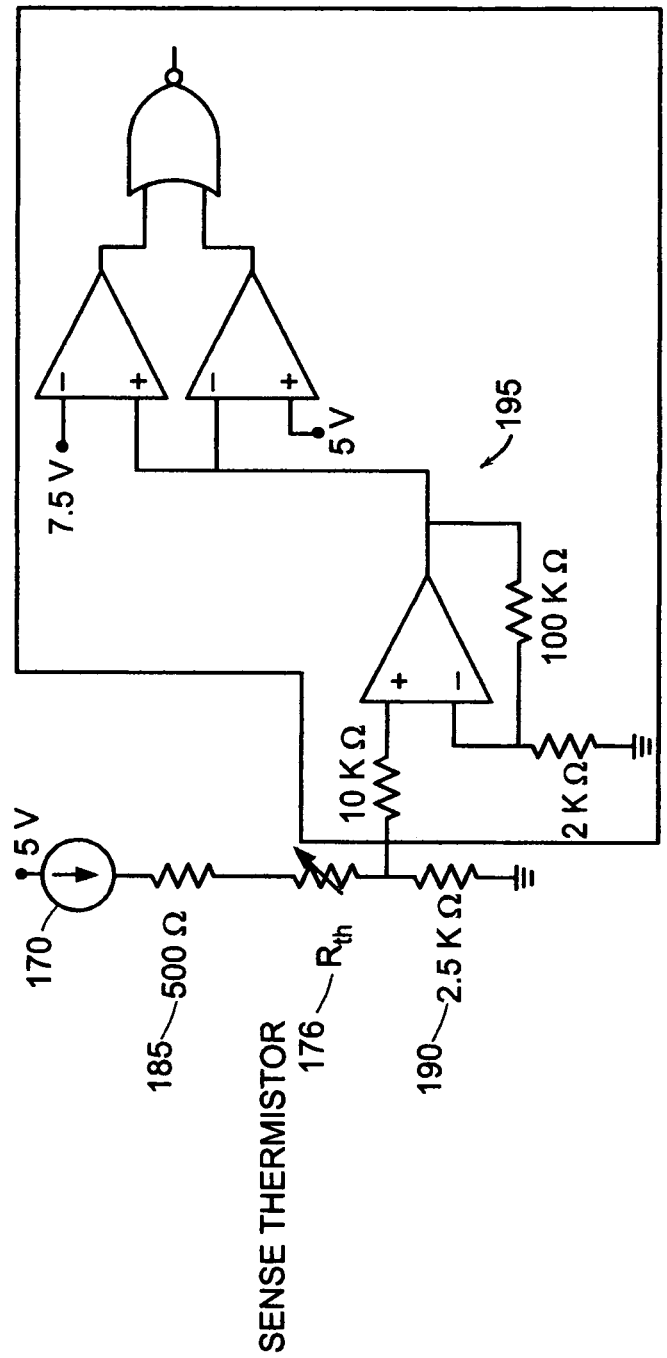
FIG. 9 is a simplified diagram of one embodiment of another circuit used in a control circuit.

FIG. 9 shows a schematic of an embodiment of a thermal sensor and safety circuit that comprises another part of the control circuit of the Detector Circuit 54 as shown in FIG. 7. The thermal sensor and safety circuit consist of a current source 170 for measuring the temperature with the second or sense thermistor 176 of the probe 64 (FIG. 7); a set of calibration resistors 185, 190; and a safety circuit 195 that gives a signal or terminates operation if the voltage applied to thermistor 176 is outside of a preset range. The second thermistor 176 connects through the connector 53 shown in FIG. 1.

As perfusion measurements are being taken and time passes, physiological, sensor and instrument conditions change and recalibration is necessary. Referring again to FIGS. 3 and 4, the physiological or sensor and instrument artifact conditions are examples of conditions that may change and affect established baseline conditions. One or more such conditions are monitored and recalibration is initiated when a value or values associated with these monitored conditions fall outside of a predetermined range.

In the mode of FIG. 3, physiologic conditions are monitored and when the resulting value or a weighted combination of values fall within a predetermined range, that is when the monitored conditions do not materially affect or degrade accuracy, recalibration is not thereby indicated. One or more measurement artifact conditions are also monitored and when the resulting value or weighted combination of these values are within a preset acceptable range, that is when perfusion measurement accuracy is not materially affected or degraded by artifact conditions, recalibration is again not indicated. Perfusion measurements are deemed reliable.

When either or both of the values resulting from measurement of one or more physiologic conditions and the values resulting from measurement of artifact conditions fall outside of the preset ranges, indicating a degradation of accuracy of the perfusion measurements, recalibration is indicated. The perfusion sensor is calibrated in response to a degradation of accuracy due to physiologic conditions and the instrument is calibrated in response to a degradation of accuracy due to sensor or instrument artifact conditions that adversely affect perfusion measurement. Calibration and recalibration may be initiated manually in response to a signal provided by the system or initiated automatically by the system.

In the mode of FIG. 4, one or more physiologic, sensor and instrument conditions are monitored. When the resulting value or values are within an acceptable range, indicating reliability of perfusion measurements, perfusion measurements are made. When the resulting value or values are outside of the acceptable range additional inquiry is indicated. The system determines if instrument conditions contribute a substantial component to the degradation. If not, recalibration in situ of the perfusion sensor is indicated. If so, recalibration of the instrumentation is indicated. Calibration and recalibration of the sensor and/or the instrumentation may be initiated manually in response to a signal provided by the system or initiated automatically by the system.

The present invention is described above in terms of specific embodiments. It is anticipated that other uses alterations and modifications will be apparent to those skilled in the art given the benefit of this disclosure. It is intended that the following claims be read as covering such other uses alterations and modifications as fall within the true spirit and scope of the invention.

The invention claimed is:

1. Apparatus for determining the perfusion of blood in living tissue comprising:
    means in thermal contact with tissue in a capillary bed for sensing the reference temperature of the capillary bed when the capillary bed is unheated;
    means in thermal contact with the capillary bed for heating the capillary bed;
    means for applying power to said heating means sufficiently rapidly to raise the temperature of said heating means to a temperature above said reference temperature so that the power necessary to maintain said heating means temperature varies as a function of time;
    means for determining the temperature difference between said heating means temperature and said reference temperature, means for determining the resistance of said heating means at said heating means temperature and means for determining the time varying relationship between the power required to maintain said heating means at said heating means temperature after said temperature has been reached and the time during which said power is being applied thereto;
    a data processor responsive to said temperature difference, said heating means resistance and said time varying power and time relationship for determining a perfusion related value; and
    means for evaluating conditions that affect the reference temperature of the capillary bed and recognizing conditions under which the reference temperature is no longer valid; and means for providing an output in response to said evaluating and recognizing means.

2. Apparatus according to claim 1 further comprising means for automatically calibrating said sensing means in response to said output.

3. Apparatus according to claim 1 wherein said recognizing means comprises means for recognizing one or more physiological and artifactual conditions.

4. Apparatus according to claim 3 wherein the artifactual conditions comprise one or more of:
    ambient temperature changes,
    electrical interference,
    instrumentation drift,
    excessive sensor-tissue contact force that can induce capillary collapse,
    insufficient sensor-tissue contact force that can result in artifactual transduction of perfusion,
    sensor cross-talk, and
    motion of the sensor relative to the tissue.

5. A system according to claim 3 wherein the physiological conditions comprise one or more of:
    tissue and vascular damage,
    tissue edema,
    tissue scar formation,
    influence of a large vessel,
    change in vascular status,
    changes in perfusion,
    changes in blood pressure,
    changes in tissue pressure, changes in tissue temperature,
changes in blood temperature, and
changes in tissue metabolism.

6. Apparatus for determining the perfusion of blood in living tissue comprising:
   means adapted to contact tissue for sensing a reference temperature of the tissue when the tissue is unheated;
   a heating element for heating tissue including tissue contacted by said heating element, said heating element having a predetermined thermal conductivity and a predetermined thermal diffusivity;
   means for applying power to said heating element sufficiently rapidly to raise the temperature of said heating element above said reference temperature so that the power necessary to maintain said heating element temperature varies as a function of time;
   means for determining the temperature difference between said heating element temperature and said reference temperature, means for determining the resistance of said heating element at said heating element temperature and means for determining the time varying relationship between the power required to maintain said heating element at said temperature after said temperature has been reached and the time during which said power is being applied thereto;
   a data processor responsive to said temperature difference, said heating element resistance, said applied power in accordance with said time varying power and time relationship, said predetermined thermal conductivity and/or diffusivity of said heating element, and a change in said reference temperature for determining the thermal conductivity and/or the thermal diffusivity of the tissue;
   means for computing the perfusion of blood in the tissue as a function of the thermal conductivity and/or the thermal diffusivity of the tissue; and
   means for evaluating conditions that affect the reference temperature of the tissue and recognizing conditions under which the reference temperature is no longer valid; and means for providing an output in response to said evaluating and recognizing means.

7. Apparatus in accordance with claim 6, wherein said sensing means and said heating element comprises a single element capable of sensing the temperature of the tissue and of heating the tissue.

8. Apparatus in accordance with claim 7 wherein said single element is a thermistor bead element.

9. Apparatus in accordance with claim 7, and further including means for maintaining said heating element temperature at a fixed, predetermined value above said reference temperature, said reference temperature being determined and said heating element temperature being maintained over a relatively short time interval during which said reference temperature remains substantially constant whereby said temperature difference and the resistance of said heating element also remain substantially constant.

10. Apparatus in accordance with claim 6, wherein said heating element and said sensing means comprise respectively
   a first element adapted to be immersed at a first region of the tissue for heating the first region of the tissue; and
   a second element adapted to be immersed at a second region of the tissue sufficiently remote from said first region as to be not materially affected by the heating of said first element.

11. Apparatus in accordance with claim 10 wherein said first and second elements are thermistor bead elements.

12. Apparatus in accordance with claim 10, for use over a relatively long time period during which said reference temperature varies with time and wherein said second element determines said reference temperature over said time period; and further including means for maintaining said first element temperature and the resistance of said first element at said first element temperature at fixed predetermined values over said time period during which said reference temperature varies whereby the temperature difference there between varies over said time period.

13. Apparatus in accordance with claim 10, for use over a relatively long time period during which said reference temperature varies with time wherein said second element determines said reference temperature over said time period; and further including
   means for determining the first element temperature over said time period as a function of said reference temperature and a preselected fixed value of said temperature difference;
   means for maintaining the resistance of said first element over said time period at a value such as to maintain the temperature difference between said first element temperature and said reference temperature at said preselected fixed value, said resistance varying as a function of time; and
   means for determining the thermal conductivity of the tissue over said time period as a function of said temperature difference, said resistance of said first element, the power applied to heat said first element and said thermal conductivity of said first element.

14. Apparatus in accordance with claim 13, wherein said data processing system includes
   means for determining the intrinsic thermal conductivity $k_m$ of the tissue when no fluid is flowing therein;
   means for determining the effective thermal conductivity $k_{eff}(t)$ of the tissue when a fluid having a predetermined heat capacity is flowing therein;
   means for determining the ratio of $k_{eff}(t)/k_m$ over said time period; and
   means for determining the rate of flow $\omega(t)$ of said fluid in the tissue as a function of said ratio.

15. Apparatus in accordance with claim 10, for use over a relatively long time period during which said reference temperature varies with time wherein said second element determines said reference temperature over said time period; and further including
   means for determining the resistance of said second element over said time period;
   means for determining the desired resistance of said first element over said time period as a function of the resistance of said second element and of a preselected fixed value of the resistance difference between the resistances of said second and said first elements;
   means for maintaining the resistance of said first element at said desired resistance so that said resistance difference is maintained at said predetermined fixed value, the resistance of said second element varying as a function of time;
   means for determining the temperature of said first element over said time period at said desired resistance of said first element, said temperature varying as a function of time;
   means for determining the temperature difference between said first element temperature and said reference temperature over said time period, said temperature difference varying as a function of time; and means for determining the thermal conductivity of the tissue over said time period as a function of said temperature difference, said resistance of said first element, the power applied to heat said first element and the conductivity of said first element.

16. Apparatus in accordance with claim 15, wherein said data processing system includes
   means for determining the intrinsic thermal conductivity $k_m$ of the tissue when no fluid is flowing therein;
   means for determining the effective thermal conductivity $k_{\mathit{eff}}(t)$ of the tissue when a fluid having a predetermined heat capacity is flowing therein;
   means for determining the ratio of $k_{\mathit{eff}}(t)/k_m$ over said time period; and
   means for determining the rate of flow $\omega(t)$ of said fluid as a function of said ratio.

17. Apparatus according to claim 6 wherein said evaluating and recognizing means comprises means for recognizing one or more physiological and artifactual conditions.

18. Apparatus according to claim 17 wherein the artifactual conditions comprise one or more of:
   ambient temperature changes,
   electrical interference,
   instrumentation drift,
   excessive sensor-tissue contact force that can induce capillary collapse,
   insufficient sensor-tissue contact force that can result in artifactual transduction of perfusion,
   sensor cross-talk, and
   motion of the sensor relative to the tissue.

19. A system according to claim 17 wherein the physiological conditions comprise one or more of:
   tissue and vascular damage,
   tissue edema,
   tissue scar formation,
   influence of a large vessel,
   change in vascular status,
   changes in perfusion,
   changes in blood pressure,
   changes in tissue pressure,
   changes in tissue temperature,
   changes in blood temperature, and
   changes in tissue metabolism.

* * * * *